United States Patent [19]
Overton

[11] Patent Number: 5,846,292
[45] Date of Patent: Dec. 8, 1998

[54] CHROMATOGRAPH WITH COLUMN EXTRACTION

[75] Inventor: Edward B. Overton, Baton Rouge, La.

[73] Assignee: Board of Supervisors at Louisiana State University & Agricultural & Mechanical College, Baton Rouge, La.

[21] Appl. No.: 852,255

[22] Filed: May 6, 1997

[51] Int. Cl.$^6$ ................................................. B01D 15/08
[52] U.S. Cl. .................................... 95/86; 95/87; 96/102; 96/104
[58] Field of Search ................................ 73/23.25, 23.26, 73/23.35, 23.36, 23.39, 23.42; 95/82–89; 96/101–107

[56] References Cited

U.S. PATENT DOCUMENTS

| | | | |
|---|---|---|---|
| 3,053,077 | 9/1962 | Tracht | 73/23 |
| 3,062,039 | 11/1962 | Ayers | 73/23 |
| 3,366,149 | 1/1968 | Taft et al. | 141/82 |
| 3,537,585 | 11/1970 | Waters | 210/198 |
| 3,668,834 | 6/1972 | Deans | 55/67 |
| 4,269,608 | 5/1981 | Sisti et al. | 55/67 |
| 4,383,839 | 5/1983 | Sisti et al. | 96/105 X |
| 4,650,964 | 3/1987 | Vincent | 219/301 |
| 4,728,776 | 3/1988 | Vincent | 219/301 |
| 4,805,441 | 2/1989 | Sides et al. | 73/23.1 |
| 4,948,389 | 8/1990 | Klein et al. | 55/20 |
| 5,005,399 | 4/1991 | Holtzclaw et al. | 73/23.39 |
| 5,014,541 | 5/1991 | Sides et al. | 73/23.41 |
| 5,028,243 | 7/1991 | Rubey | 55/67 |
| 5,047,073 | 9/1991 | Stetter et al. | 55/18 |
| 5,048,322 | 9/1991 | Hiller et al. | 73/23.41 |
| 5,096,471 | 3/1992 | Sacks et al. | 55/67 |
| 5,215,556 | 6/1993 | Hiller et al. | 96/101 X |
| 5,492,838 | 2/1996 | Pawliszyn | 436/178 |
| 5,588,988 | 12/1996 | Gerstel et al. | 96/101 |
| 5,611,846 | 3/1997 | Overton et al. | 96/102 |

FOREIGN PATENT DOCUMENTS

| | | | |
|---|---|---|---|
| 20622110 | 6/1971 | France | 96/101 |

OTHER PUBLICATIONS

Grote, et al. Solid–Phase Microextraction for the Analysis of Human Breath, pp. 587–596, Analytical Chemistry, Feb. 15, 1997.

Klemp, et al. Cryofocusing Inlet with Reverse Flow Sample Collection for Gas Chromatography, pp. 2516–2521, Analytical Chemistry, Sep. 15, 1993.

Carney, et al. Use of a Microchip Gas Chromatograph for Ambiant Air Analysis, pp. 21–37, Sampling and Analysis of Airborne Pollutants, 1993.

Overton, et al. Proof of Concept: Microchip Gas Chromatograph with In–Line Sample Concentration Suitable for Use with Ion Mobility Spectrometry, Jun. 21, 1991.

Brochure from Sentex Systems, Inc. on Portable Gas Chromatograph (Unknown Date and Author).

Muller, Analytical Application; Note No. 282 from the Siemens Company (Unknown Date).

Muller, Analytical Application; Note No. 297 from the Siemens Company (Unknown Date).

*Primary Examiner*—Robert Spitzer
*Attorney, Agent, or Firm*—Kean, Miller, et al.; Russel O. Primeaux; Morgan E. Malino

[57] ABSTRACT

A gas chromatograph and method of chromatography are provided. Analytes, those compounds to be tested, are extracted from the sample by moving the sample into a column which has a stationary phase along the column walls. The column has two sections which are different in length. The longer section is heated and the analytes move to the shorter section. The longer section is then cooled and the entire column is heated. The device then functions as an analytical column and the analytes move out of the shorter section, through the longer section, and out of the column. A detector placed at the end of the column's longer section detects the presence of the compounds as they exit the column. In an alternate embodiment two separate columns are provided. One column is used as the extraction column and the other is used as the analytical column.

20 Claims, 4 Drawing Sheets

CHROMATOGRAPH WITH COLUMN EXTRACTION

BACKGROUND OF THE INVENTION

1. Field of the Invention

This invention relates, generally, to analyses using devices for liquid and gas chromatography, and particularly to portable chromatographic devices and analyses.

2. Prior Art

Chromatography is the group of laboratory separation techniques in which a mobile phase (either a gas or liquid) is flowed over a stationary phase (either liquid or solid). As the mobile phase moves past the stationary phase, repeated adsorption and desorption of the solute occurs at the rate determined chiefly by the solute's ratio of distribution between the two phases (partition ratio, K).

A gas chromatograph (GC) is an analytical instrument which uses the principle discussed above to separate and identify the solute compounds as a gas that are present in a sample. Typical GC analysis will include: (1) an extraction step external of the GC instrument in which the sample is obtained and the analytes are extracted from the sample; (2) an injection step in which the analytes are injected into the GC instrument, converted into the gaseous state, and moved to the head of an analytical column; (3) a separation step in which the analytical column separates the extracted mixture into its individual components as they are moved through the column by an inert carrier gas (mobile phase), and (4) a detection step in which the components are detected as they exit the analytical column.

The device which is used to obtain the sample of the gas, liquid or solid to be analyzed may be either separate from or integrated with the GC device. In some devices, the sample is drawn into a sample trap or loop which contains representative quantities of the analytes. In other devices a wick type device (solid phase microextraction) is used to extract the analytes from the sample, and then the analytes from the wick are volatilized when heated and flowed into the GC for separation. Liquid/liquid extraction can also be used for aqueous samples and is used for solid samples. A shortcoming of the above methods of extracting a sample is that they require an extraction assembly which is separate and apart from the component which does the actual separation, the analytical column.

There are myriad applications for small portable GCs to include: the analysis of petroleum hydrocarbons and petrochemicals for industrial process monitoring and pollution detection; prevention of terrorist activities by field detection of chemical warfare agents and plastic explosives in bombs; field detection of drugs of abuse; real time detection of hazardous chemicals from industrial and transportation accidents; exploration for petroleum using detection of marker compounds in ground gas; detection of product quality based on analysis of odors and other chemicals that indicate composition or contamination; and medical diagnosis based on detection of indicator chemicals in breath and body fluids.

In traditional GC analysis the extraction and analysis functions are not performed by the same instrument or even at the same time. This separation of the extraction and analysis functions is time consuming, makes for higher costs, and can lead to analytical errors because of the increased handling of the extracts. Additionally, having separate extraction and analysis functions creates a process which is not readily amenable to automation or computer control.

The elimination of unnecessary components and the dual use of other components would reduce the weight of the device and would also reduce size and power consumption. Elimination of components can also reduce the number of fluid connections in the GC. These components tend to be heat sinks and can serve to skew the accuracy of testing.

Some advances have been made in the field to allow for smaller gas chromatographs. U.S. Pat. No. 5,611,846 to Overton et al discloses a GC which uses electrical resistive heater wire placed adjacent to the analytical column for heating of the column. This configuration allows for a device of less bulk than conventional oven GCs. However, even the device of the '846 Patent uses an extraction and injector assembly which is separate and apart from the analytical column.

OBJECTS OF THE INVENTION

It is an object of the present invention to provide a GC-based analytical device and method which eliminates the extraction and injection components as separate components of the GC device.

Another object of the present invention is to provide a GC-based analytical device which is lighter in weight than conventional GCs.

Another object of the present invention is to provide a device which reduces the number of control valves that are found in a conventionally configured GC.

Another object of the present invention is to provide a device and method which eliminates the backflushing of components as a separate step in the chromatography process.

Another object of the present invention is to provide a GC which is easier to manufacture.

Another object of the present invention is to provide a GC which will use the entire extracted sample in the analysis.

SUMMARY OF THE INVENTION

A device is provided for chromatographic analysis. The new chromatograph includes a continuous column having two fluidly connected sections, with the first section being longer than the second section. The temperature of each section can be independently controlled.

A carrier gas source is connected to the ends of the column, and there is a valve at each end of the column. A detector is placed at one end of the column. The column sections can be programmed to heat up to specific temperatures above ambient temperature at specific rates, and to cool down to ambient temperature or a higher temperature.

The sample (either gaseous or liquid) is taken in at one section of the column while the column is maintained at low (ambient) temperature. The stationary phase on the column's internal walls acts as an extraction medium for removing analytes from the sample. After passing the sample through the column, the column is purged with carrier gas and the extracted analytes remain.

The first section of the column, which is longer than the second section, is heated while the carrier gas is flowed from the first section to the second section. As the analytes are heated they volatilize and move to the second shorter section, where they condense and attach to the stationary phase in the second section in a relatively narrow band. The first section is then cooled.

The entire column is then heated using temperature programming techniques and the carrier gas is flowed from the second shorter section to the first longer section. As the column is heated the analytes move selectively and exit the column out of the first longer section. The exiting analytes pass through a detector which detects the compounds as they move out of the column.

A feature of the novel GC device is that it uses less power than a conventionally configured GC.

An additional feature of the novel GC device is that it can be completely automated.

An additional feature of the invention is that because it provides fewer control valves and other connections, it reduces the number of heat sinks in the GC device.

An additional feature of the invention is that it is more reliable because it eliminates steps in the extraction and analysis process.

These and other objects, advantages, and features of this invention will be apparent from the following descriptions of the invention.

DETAILED DESCRIPTION OF THE PREFERRED EMBODIMENTS

Figure 1A:
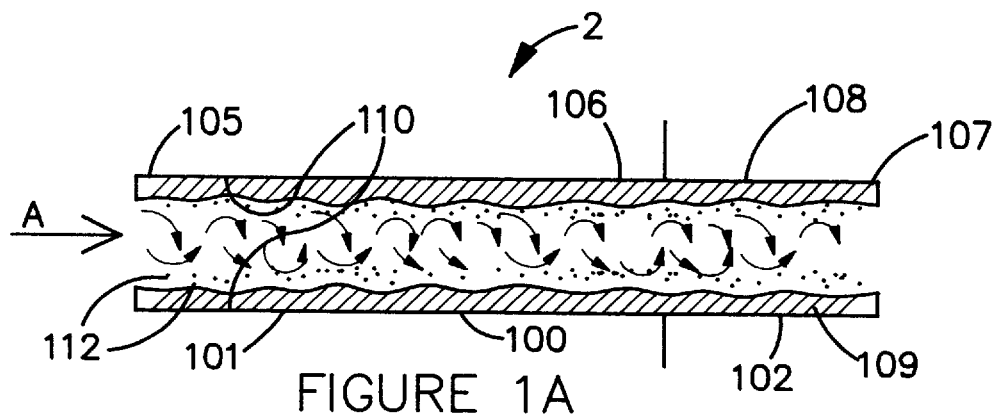
FIGS. 1A–1D are schematic views of the invention.

The inventor believes the essence of the invention is the use of a column with a stationary phase to perform the extraction function. The column used for extraction can be the same column used for the analysis or two columns, one for extraction and one for separation, can be employed. Referring to FIGS. 1A–1D the basic operation of the invention will be explained.

FIGS. 1A–1D show one embodiment of chromatograph 2 which will include analytical column 100. Analytical column 100 includes first section 101 and second section 102 which are fluidly connected and form continuous analytical column 100. First section 101 will have its own temperature adjustment means 103 and second section 102 will have its own temperature adjustment means 104. First and second section temperature adjustment means 103, 104 are not shown in FIG. 1A, only in FIGS. 1B–1D.

First section 101 has free end 105 and connecting end 106; second section has free end 107 and connecting end 108. Connecting ends 106, 108 are fluidly connected to each other to form continuous analytical column 100. Stationary phase 109 is alongside column walls 110. Stationary phase 109 will be either a solid or a liquid for chromatographic separations. Chromatograph 2 will include detector 111 which can be used to indicate the presence and amount of the compounds exiting first section free end 105.

In FIG. 1A the sample is being drawn into column 100 via first section free end 105 by one of two methods. In one method a vacuum is placed on second section free end 107. In another method the sample is pumped into first section free end 105. The pumping method is preferred because with it a greater pressure differential can be achieved along the length of column 100.

As shown in FIG. 1A the carrier gas together with the sample is brought into column 100 in Direction "A." As the sample moves into column 100, analytes 112, those compounds which are to be analyzed, will be extracted by stationary phase 109 in both first and second sections 101, 102. Once a sufficient amount of the sample has been pumped into column 100, no more sample will be pumped into column 100 but the pumping of the carrier gas will continue until all of the sample matrix has been discharged from second section free end 107, leaving only analytes 112 in column 100.

The entire first step just described in which the sample is flowed into column 100 is preferably performed at ambient temperature. Once the sample matrix has been discharged from second section free end 107 the step depicted in FIG. 1B will be performed. In this second step first section 101 is heated according to temperature programming techniques using first section temperature adjustment means 103 as the carrier gas flow is continued into first section free end 105 and out of second section free end 107.

As first section 101 is heated, analytes 112 will convert to the gaseous state and move to second section 102. When analytes 112 arrive in cooler section 102 they condense and attach to stationary phase 109 along column walls 110 in a relatively narrow band.

Figure 1B:
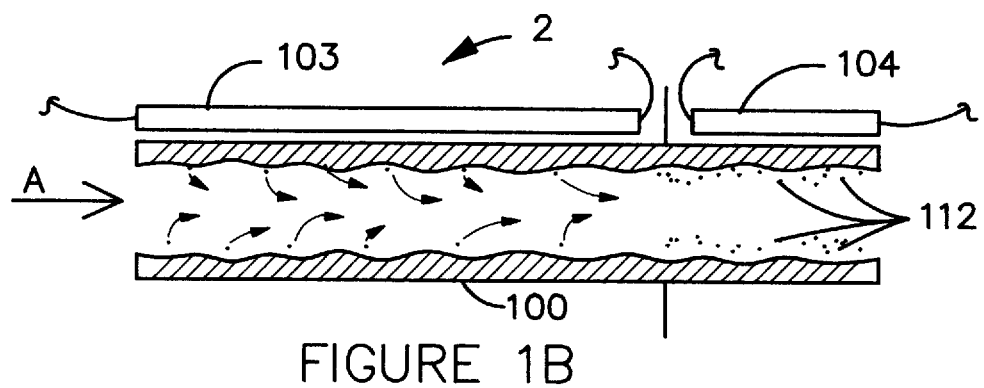
Figure 1C:
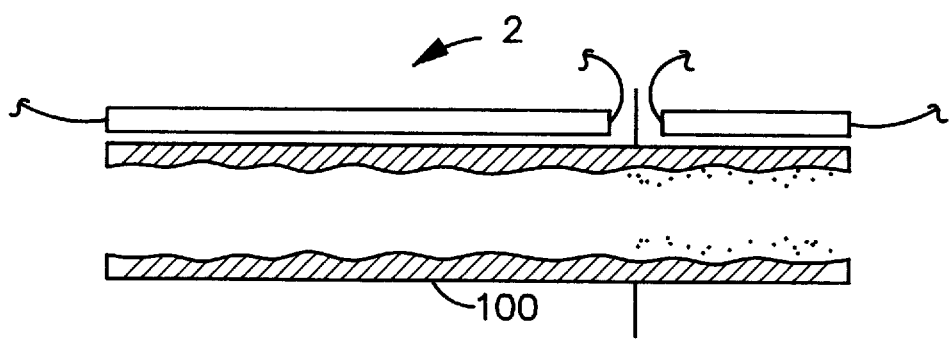

FIG. 1C depicts the next step of the process. After substantially all of analytes 112 have moved into second section 102, first section 101 is cooled using first section temperature adjustment means 103. During this step it is not necessary to continue the flow of the carrier gas through column 100. However, it may be preferable to continue the flow in Direction "A" so as to assist in the cooling of first section 101. When the cooling of first section 101 is complete first section 101 will be at substantially the same temperature as second section 102.

Although throughout the description of the device, reference is made to the heating of the sections, it is to be understood that the key to moving analytes 112 from first section 101 to second section 102 is the relative temperature differences between the sections. Those skilled in the art could cool one section of the column or heat the other to achieve the requisite temperature differential. The technique selected will also depend on the analyte and the temperature at which it vaporizes.

Figure 1D:
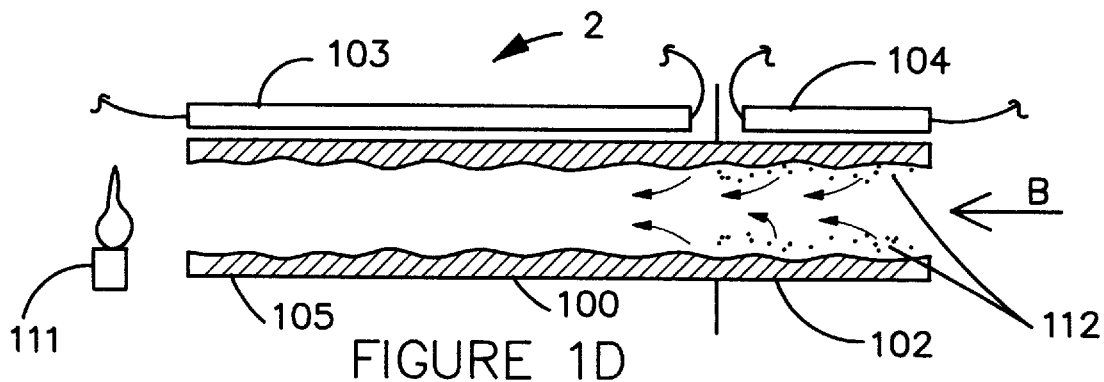

In the final step shown in FIG. 1D column 100 functions much like a conventional analytical column. Using both first section and second section temperature adjustment means 103, 104 column 100 is heated along its entire length according to a selected temperature program. As column 100 is heated the carrier gas is flowed into column 100 at second section free end 107 in Direction "B." Alternatively, one could flash heat second section 102 and heat first section 101 using temperature programming.

In this final step analytes 112 in section 102 are converted into the gaseous state and move out of second section 102 toward first section free end 105. As analytes 112 move selectively out of first section free end 105 they are detected by detector 111. The heating of column 100 and the flow of carrier gas in Direction "B" is continued until substantially all of analytes 112 have been eluted from column 100. Column 100 can then be cooled and the cycle can begin again with the intake step shown in FIG. 1A.

Figure 2:
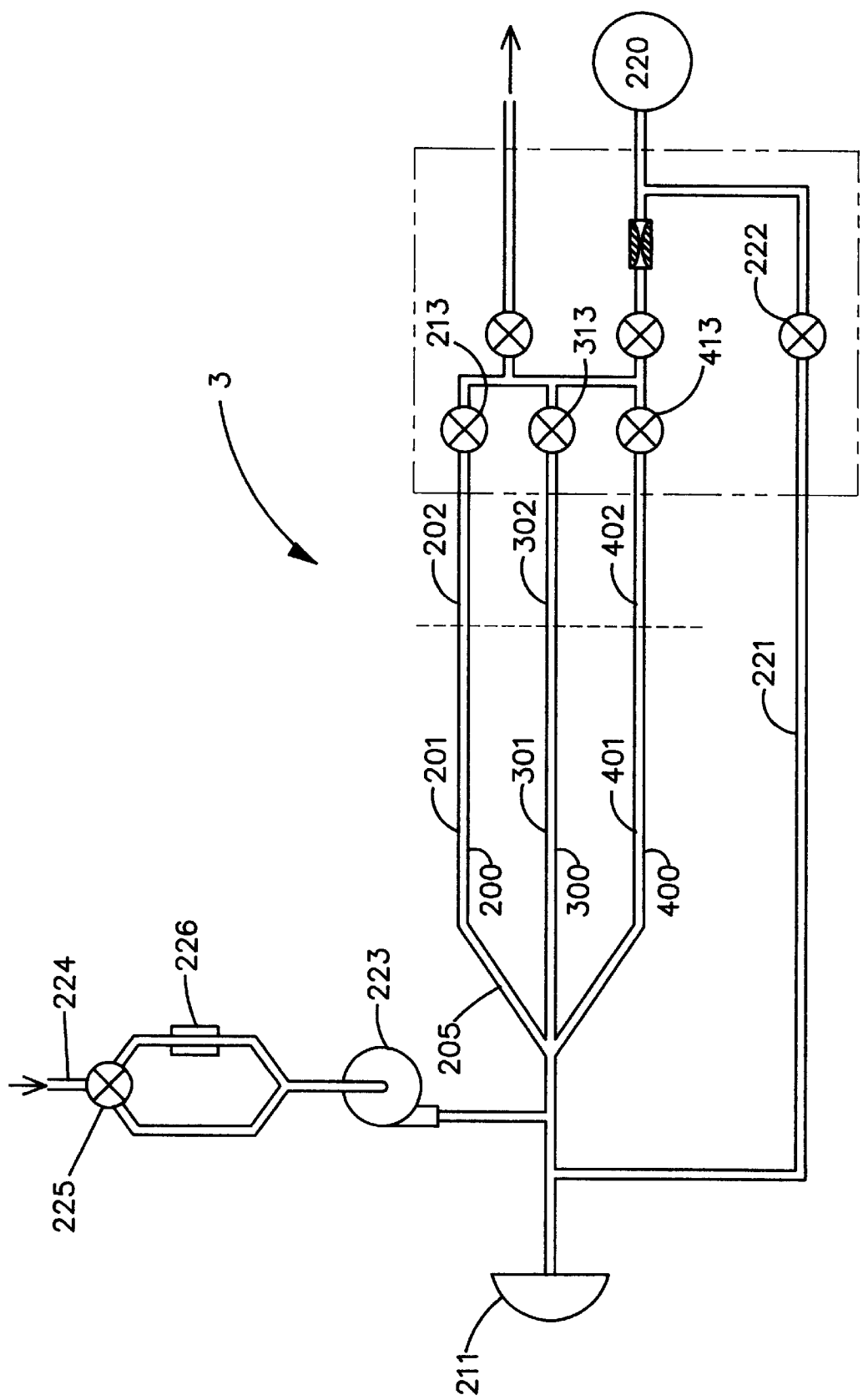
FIG. 2 is a schematic view of a preferred embodiment of the invention in which three columns are provided.

It can be seen that the apparatus and process just described eliminates the need for a separate extraction and injection assembly because chromatograph 2 uses column 100 for both extraction and separation. First section 101 will be longer than second section 102. The proportions and relative lengths of first section 101 and second section 102 as depicted in FIGS. 1–1D and FIG. 2 are not to scale. It is preferred that the ratio of the actual length of first section 101 to second section 102 be approximately 100 to 1 so as to achieve a narrow band of analyte accumulated in second section 102 prior to the final separation step.

FIG. 2 shows a preferred embodiment of the invention, multi-column chromatograph 3. For all three digit numbers in the 100 to 400 series the item identified will be the same as other items with the same last two digits. Multi-column chromatograph 3 will include columns 200, 300, 400 which are different in diameter, length, or liquid phase, or combinations thereof.

These multiple columns 200, 300, 400 will allow for the targeted analysis of particular families of compounds and will eliminate the need for the use of separate GCs to test for multiple compounds. A single column arrangement is limited in that it cannot extract and analyze a broad range of both volatile and semi-volatile analytes. A device with several columns can be designed so that each column is adapted to handle compounds with a specific range of volatilities and polarities. By using a multi-column device comprehensive analysis of samples can be performed.

Plurality of columns 200, 300, 400 will each have first section 201, 301, 401 and second section 202, 302, 402. Descriptions will only be given for column 200 and its related components but the same descriptions will apply to columns 300 and 400. While only three columns are depicted, one could have one or two columns, or any number of columns.

Carrier gas source 220 is connected to first section free end 205 via reverse flow line 221 and carrier gas valve 222. Also connected at first section free end 205 is intake pump 223. The sample will be drawn in at sample inlet 224 via pump intake pump 223 into first section free end 205. Those skilled in the art will be familiar with other methods of bringing the sample into column 200. For example, the samples could be placed in a flexible or rigid vessel which is fluidly connected between intake pump 223 and first section free end 205, and the carrier gas could be pumped through the vessel into column 200 until the vessel is purged.

Optional adsorption trap 226 will act as a scrubber to ensure that the air routed to detector 211 is free of the very compounds which are being tested. If these compounds are not removed from the air supply to the detector they can cause inaccurate readings at the detector. The use of a scrubber such as adsorption trap 226 eliminates the need for a separate source of air for detector 211, which would increase the size and weight of the device and make it less desirable for use in the field. The trap can also be used as a concentrating trap for detection of analytes at very low concentrations.

Inlet valve 225 can be set to allow flow directly into columns 200, 300, or 400 during sample intake or inlet valve 225 can be set to direct the flow of air via adsorption trap 226 to detector 211 during the separation phase. Each column will have a terminal control valve 213, 313, 413 which will allow the flow from columns 200, 300, 400 out to atmosphere during the process steps depicted in FIGS. 1A and 1B.

For the embodiment depicted in FIG. 2 a flame ionization detector (FID) is used as detector 211. However, those skilled in the art could instead use other detectors such as photo-ionization, helium ionization, argon ionization, RF-coupled helium ionization, micro-thermal conductivity, electron capture, halide specific, ion mobility spectrometer, mass spectrometer, direct field ionization, flame photometric, pulsed flame photometric, or photoinduced photoemission detectors.

The heater wire embodiment of first section temperature means 103 and second section temperature means 104 is shown in FIGS. 1B–1D. In a preferred embodiment chromatographs 2 and 3 will use two separately controllable and programmable electrical-resistive heater wires, one for the first section and one for the second section, which run alongside the column. The heater wire configuration is desirable because it is a low thermal mass system. A low thermal mass system is favored because it allows for rapid cooling and heating of the column sections. An additional advantage of the heater wire system over conventional oven GCs is the smaller size of the heater wire system.

U.S. Pat. No. 5,611,846 to Overton et al (the '846 Patent), is hereby incorporated by reference in its entirety into this current application. The '846 Patent discloses a heater wire configuration which can be adapted to this current application. Additionally, the '846 Patent discloses techniques and devices related to temperature programming, techniques and devices which may also be adapted to this current application.

Those skilled in the art may want to heat and cool the column sections in other ways. For example, one could use two adjacent ovens which share a common wall, with first section 101 in one oven, and second section 102 in a second oven. Alternatively, one could use a single oven which contains the entire column, but second section 102 could be insulated and wholly disposed within the oven and be cooled by passing a cryogenic or other cooling fluid coolant through a jacket which surrounds second section 102.

The inventor believes the novelty of the invention lies in the use of a column, with a stationary phase along its walls, to extract the analytes as the sample, which is the mobile phase, is moved through the column. This technique has the added advantage of allowing the analytical column to also serve as an extraction column.

Figure 3:
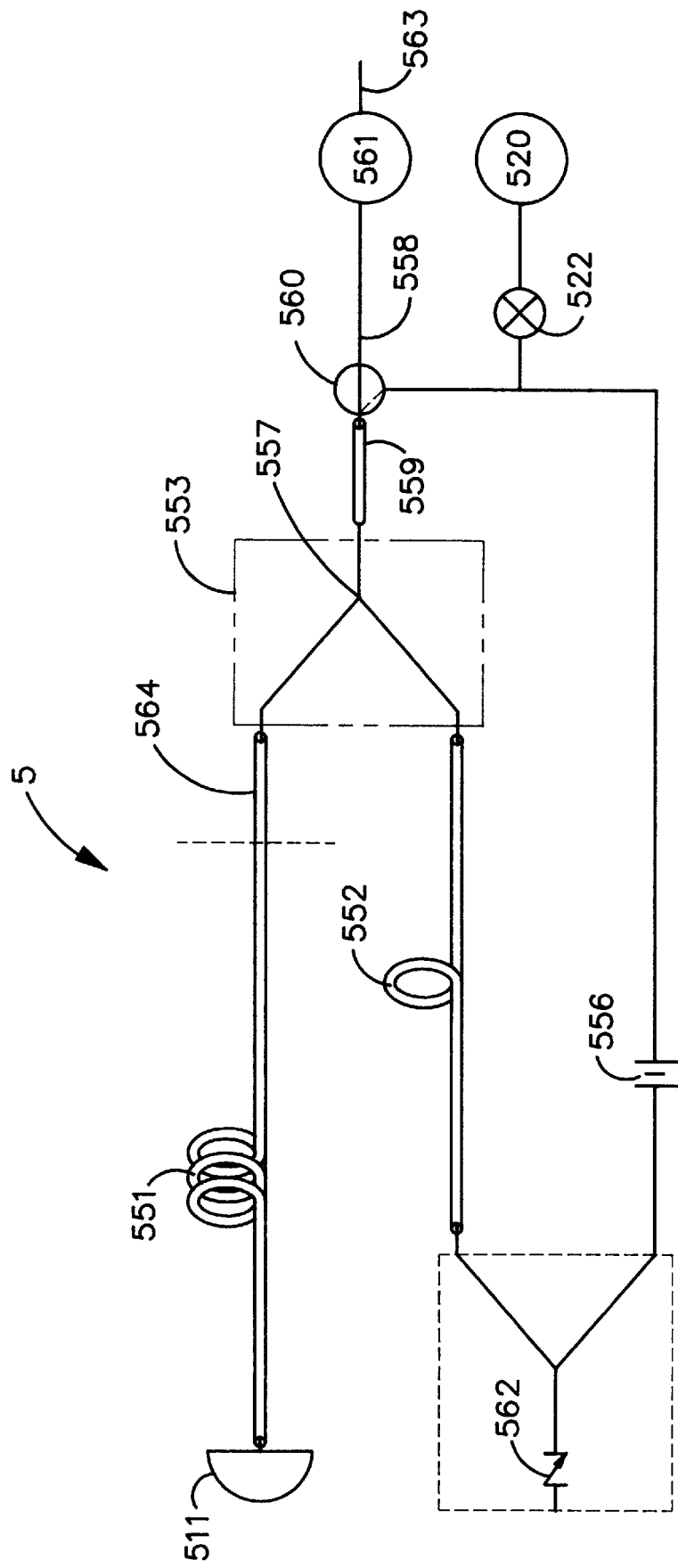
FIG. 3 is a schematic view of another embodiment of the invention which uses a separate column as an extraction device.

However, one may want to use one column for extraction and another for separation. FIG. 3 depicts such an embodiment. Chromatograph 5 will include the following major components: analytical column 551, extraction column 552, heated zone 553, detector 511, and carrier gas source 520.

The sample is brought into extraction column 552 via inlet check valve 562 by vacuum pump 561. The entire device will be at ambient temperature during sample intake. Although there is no valve closing off extraction column 552 from analytical column 551, the difference in diameters and lengths of the columns is such that the sample (the sample matrix) will be drawn into extraction column 552.

The diameter of extraction column 552 is chosen for flow and is relatively large because it is only used for extraction; whereas the diameter of analytical column 551 is chosen for high resolution of the analytes, and is relatively small. Analytical column 551 also has more resistance to flow than extraction column 552 because analytical column 551 is longer than extraction column 552.

As the sample is brought into extraction column 552 the analytes attach to the stationary phase in extraction column 552. Vacuum pump valve 560 is set so that the unextracted compounds of the sample (the sample matrix) will flow out of extraction column 552 through column joint 557 and vacuum pump 561 to vent 563.

Once the analytes have been extracted vacuum pump 561 is turned off. Vacuum pump valve 560 and carrier gas valve 522 are set so that inert carrier gas is flowed from carrier gas source 520 through carrier gas valve 522 into extraction column 552. Optional flow resistors 556 and 558 can be chosen so that the carrier gas will flow at the desired rate.

Extraction column 552 is heated as the carrier gas is flowed through it, preferably using temperature programming. The analytes in extraction column 552 will volatilize and move through column joint 557 into injector 559. In a preferred embodiment heated zone 553, together with column joint 557 which is disposed therein, will be heated to approximately the same temperature as extraction column 552. Doing so will prevent the premature condensation of analytes inside of column joint 557.

Injector 559 will be cooler than extraction column 552 and the analytes will condense in injector 559. Once substantially all of the analytes have moved from extraction column 552 into injector 559 extraction column 552 will cool and return to ambient temperature. Vacuum pump valve 560 will be set so that carrier gas can flow from carrier gas valve 522 via vacuum pump valve 560 into injector 559. Analytical column 551 and injector 559 will be heated according to a prescribed temperature program.

The setting of vacuum pump valve 560 will prevent the carrier gas, and the analytes carried with it, from flowing into extraction column 552. Instead the analytes will flow into analytical column 551 out to detector 511. When substantially all of the analytes have moved from injector 559 through analytical column 551 and detector 511, all of the components of chromatograph 5 can be cooled back to ambient temperature so that the cycle can begin again.

Chromatograph 5 serves to both extract samples and analyze them, and does so with minimal use of connections and valves, both of which can serve as heat sinks and thereby decrease the accuracy of a chromatograph.

Injector 559 serves as an intermediate step between extraction column 552, which is relatively large in diameter and which will contain the analytes in a broad band, and analytical column 551 which is smaller in diameter. Although it is preferable to use injector 559, one could practice the invention without injector 559.

In such an embodiment in which injector 559 is eliminated, when extraction column 552 is heated vacuum pump valve 560 will be set so that the carrier gas and the analytes carried therein must move through column joint 557 into analytical column 551. The analytes will condense in a narrow band at head 564 of analytical column 551. To prevent premature condensation of the analytes in column joint 557 it should be heated as extraction column 552 is heated.

While maintaining or increasing the temperature of extraction column 552 and column joint 557, analytical column 551 is heated using temperature programming. The flow of carrier gas is continued through analytical column 551 and the analytes will move selectively out of analytical column 551 to detector 511.

In the analysis of solid samples a separate step is usually undertaken to place the analytes from solid sample into a sample matrix which can then be taken into the chromatograph. Those skilled in the art will be familiar with these methods which include supercritical fluid extraction, thermal extraction, or accelerated solvent extraction.

Figure 4A:
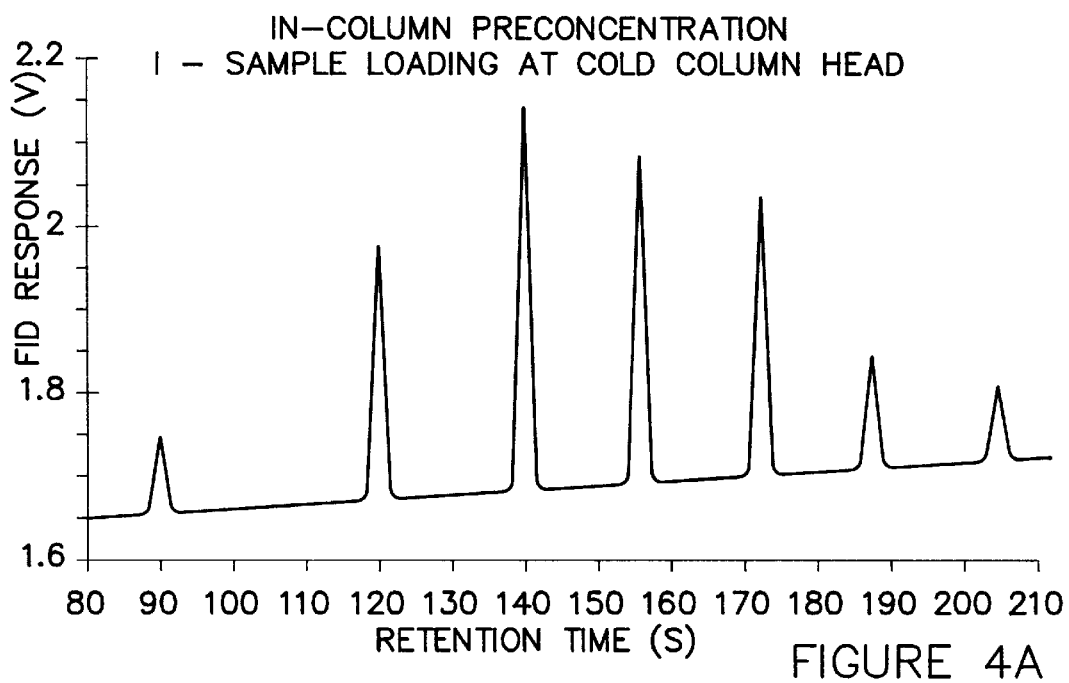
FIGS. 4A and 4B depict test results from a device made in accordance with the invention.
Figure 4B:
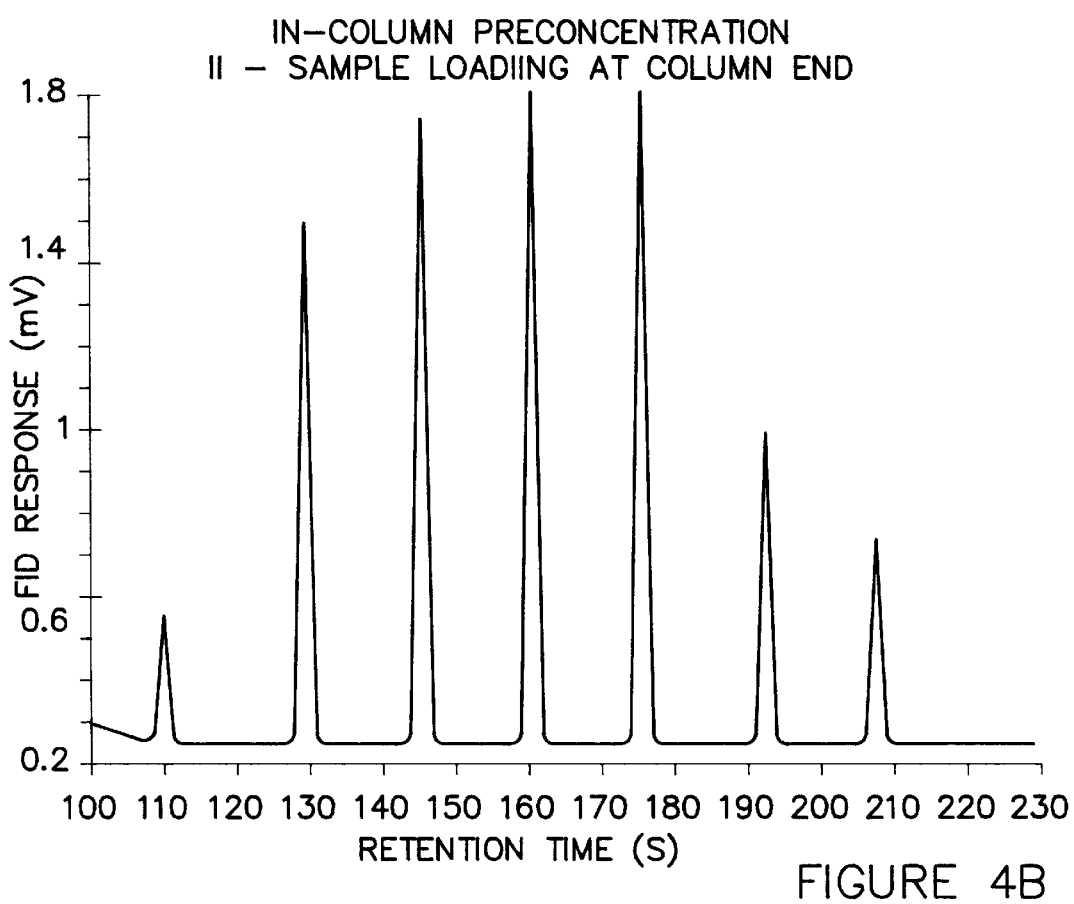

FIGS. 4A and 4B depict test results obtained from a device made in accordance with the present invention. The device was the embodiment in which a single column was used to perform both the extraction and separation functions.

A sample of gaseous hydrocarbons was made by injecting a liquid extract containing $n-C_{10}$ to $n-C_{16}$ into a heated injection port. The gas flow was directed into a one meter, 100 micron analytical column disposed in an oven. This column/oven assembly consisted of the analytical column with a sensor wire and a heater wire placed inside a 1 mm ID outer tube. The heater was designed so that a small portion of one end of the column, serving as second section 102, could be heated, or cooled with liquid $CO_2$, independently of the rest of the column and heater.

FIG. 4A shows a representative gas chromatogram obtained by passing the gaseous sample into the column through the independently heatable and coolable second section 102. Second section 102 was initially cooled as the sample was passed through the column. After focusing the analytes in second section 102, second section 102 was rapidly heated as the column was temperature programmed at 0.5° C./second from ambient to 250° C.

FIG. 4B shows a similar gas chromatogram obtained by passing the gaseous sample into first section 101 of the column. With carrier gas flowing in from first section free end 105 the column was rapidly heated to 250° C. while second section 102 was cooled with liquid $CO_2$. The analytes, extracted out of the gaseous sample, were thus moved into the second section 102 and focused into a relatively narrow band.

Flow was then reversed through the column, now flowing from second section 102 through the analytical column and into the FID detector. Second section 102 was then rapidly heated and the column temperature programmed from ambient to 250° C. at 0.5° C.

These data demonstrate the ability of the analytical column to serve as an extraction medium, a focusing medium, an injector, and a high resolution separating medium during analysis of this gaseous sample.

There are of course other alternate embodiments which are obvious from the foregoing descriptions of the invention, which are intended to be included within the scope of the invention, as defined by the following claims.

I claim:

1. A method for chromatography comprising the steps of:
   (1) providing a continuous column having a first section and a second section, said first and second sections being fluidly connected and each said section having temperature adjustment means, said first section having a free end and a connecting end, said second section having a free end and a connecting end, said connecting ends of said first and second section being connected to each other as part of said continuous column, said column having a stationary phase throughout;
   (2) flowing a sample into said column, said sample having analytes in a sample matrix;
   (3) heating said first section while flowing a carrier gas into said column via said first section free end and while venting at said second section free end such that substantially all of said analytes in said first section are moved out of said first section toward said second section;
   (4) cooling said first section;
   (5) heating said column while flowing a carrier gas into said second section free end such that substantially all of said analytes in said second section are moved through said first section and out of said column via said first section free end; and
   (6) detecting said analytes which exit said column.

2. The method in claim 1 wherein said column is at ambient temperature when said sample is flowed into said column.

3. The method in claim 1 wherein said sample is flowed into said column via said first section free end.

4. The method in claim 1 wherein:
(i) said second section has a temperature; and
(ii) when said first section is cooled in step (4), said first section is cooled to substantially the same temperature as said second section.

5. A method for chromatography comprising the steps of:
(1) providing a chromatograph comprising:
   (i) an extraction column having an inlet end and an outlet end;
   (ii) a temperature adjustment means for adjusting the temperature of said extraction column;
   (iii) an analytical column having a detector end and an inlet end, said analytical column inlet end being fluidly connected to said extraction column outlet end; and
   (iv) a temperature adjustment means for adjusting the temperature of said analytical column;
(2) flowing a sample into said extraction column, said sample having analytes in a sample matrix;
(3) heating said extraction column while flowing a carrier gas into said extraction column via said extraction column free end such that substantially all of said analytes in said extraction column are moved out of said extraction column into said analytical column;
(4) heating said analytical column while flowing a carrier gas into said analytical column inlet end such that substantially all of said analytes in said analytical column are moved out of said analytical column via said detector end; and
(5) detecting said analytes which exit said analytical column.

6. The method in claim 5 wherein:
(a) said chromatograph provided in said step (1) further comprises an injector fluidly connected to said extraction column outlet end and said analytical column inlet end;
(b) said step (3) is modified so that substantially all of said analytes are moved out of said extraction column into said injector, not said analytical column; and
(c) said step (4) is modified so that said injector and said analytical column are heated while flowing said carrier gas through said injector into said analytical column inlet end such that substantially all of said analytes in said injector are moved out of said injector into said analytical column and out of said analytical column via said detector end.

7. A chromatograph comprising:
(1) a continuous column having a first section and a second section, said first section having a first temperature adjustment means, said second section having a second temperature adjustment means, said first and second column sections being fluidly connected, said first section having a free end and a connecting end, said second section having a free end and a connecting end, said connecting ends of said first and second sections being connected to each other as part of said continuous column;
(2) a carrier gas source operably connected to said free ends;
(3) an inlet valve for controlling flow through said column via said first section free end;
(4) a terminal control valve for controlling flow through said column via said second section free end;
(5) a detecting means operably connected to said first section free end;
(6) said first temperature adjustment means for controlling the temperature of said first section; and
(7) said second temperature adjustment means for controlling the temperature of said second section.

8. The chromatograph in claim 7 further comprising a vacuum pump operably connected to said column.

9. The chromatograph in claim 7, wherein said first and second temperature adjustment means are adapted such that said first and second sections may be independently subjected to temperature programming.

10. The chromatograph in claim 7, wherein said first and second temperature adjustment means are electrical-resistive heater wires.

11. A chromatograph comprising:
(1) two or more continuous columns, each said column having a first section and a second section, said first and second column sections being fluidly connected, each said first section having a free end and a connecting end, each said second section having a free end and a connecting end, said connecting ends of said first and second sections being connected to each other as part of each said continuous column;
(2) a carrier gas source operably connected to said free ends of said columns;
(3) an inlet valve for controlling flow through said columns via said first section free ends;
(4) a terminal control valve for controlling flow through said columns via said second section free ends;
(5) a detecting means operably connected to said first section free ends;
(6) a first temperature adjustment means for controlling the temperature of said first sections of said columns; and
(7) a second temperature adjustment means for controlling the temperature of said second sections of said columns.

12. The chromatograph in claim 11 wherein:
(i) said first temperature adjustment means further comprises a separate temperature adjustment means for controlling the temperature of each said first section of each said column; and
(ii) said second temperature adjustment means further comprises a separate temperature adjustment means for controlling the temperature of each said second section of each said column.

13. The chromatograph in claim 12, wherein said first and second temperature adjustment means are adapted such that said first and second sections may be independently subjected to temperature programming.

14. The chromatograph in claim 12 wherein each said first and second temperature controlling means is an electrical-resistive heater wire.

15. The chromatograph in claim 11 wherein said first and second temperature adjustment means are electrical-resistive heater wires.

16. A chromatograph comprising:
(1) an extraction column having an inlet end and an outlet end;
(2) a temperature adjustment means for adjusting the temperature of said extraction column;
(3) an analytical column having a detector end and an inlet end, said analytical column inlet end being fluidly connected to said extraction column outlet end;

(4) a temperature adjustment means for adjusting the temperature of said analytical column.

17. The chromatograph in claim 16 further comprising:
(1 ) a column joint fluidly connecting said analytical column inlet end and said extraction column outlet end, and
(2) a carrier gas source fluidly connected to said column joint and said extraction column inlet end.

18. The chromatograph in claim 17 further comprising
(1) a vacuum pump valve connected to said column joint; and (2) a vacuum pump fluidly connected to said vacuum pump valve.

19. The chromatograph in claim 16 further comprising an inlet check valve fluidly connected to said extraction column inlet end.

20. The chromatograph in claim 16 further comprising: a detector fluidly connected to said analytical column detector end.

* * * * *